March 11, 1969 P. MERCURI ET AL Plant Pat. 2,870
CARNATION PLANT
Filed April 27, 1967
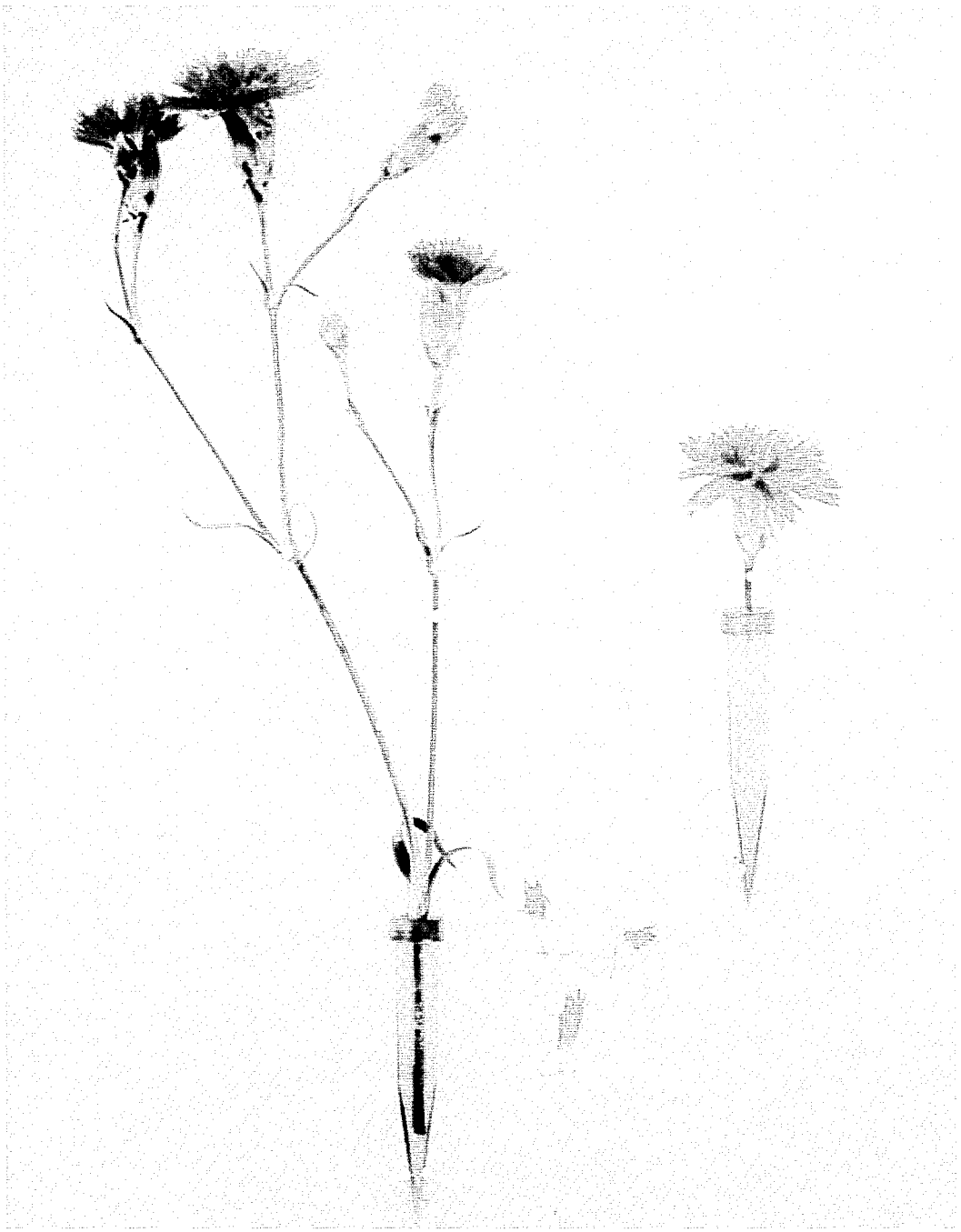

United States Patent Office

Plant Pat. 2,870
Patented Mar. 11, 1969

2,870

CARNATION PLANT

Pasquale Mercuri, 189 Post Road, and George Mercury, 260 Landham Road, both of Sudbury, Mass. 01776

Filed Apr. 27, 1967, Ser. No. 634,393
U.S. Cl. Plt.—70 1 Claim
Int. Cl. A01h *5/02*

The present invention relates to a new and distinct variety of carnation plant, which is characterized particularly by a quilled petal structure. The term, "quilled petal structure," as used herein means a petal structure having a series of ridges formed by folds of the petal which extend from the outer edge of the petal upwardly substantially to the point of attachment of the petal.

We discovered this invention as a mutation of the commercial carnation variety, "Mercury's Variegated Quill Carnation" grown commercially by us and disclosed in our co-pending application for plant patent, Ser. No. 533,732, filed Mar. 11, 1966, and entitled "Carnation Plant."

The original reproduction by cuttings was carried out by us in our greenhouses at Sudbury, Mass.

This invention may be grown as a "standard" (single bloom per stalk) or as a "miniature" (multiple bloom per stalk) with the usual commercial growing methods.

The following is a detailed description of our invention in accordance with Ridgeway's Color Standards and Nomenclature:

Parent: Mercury's Variegated Quill.

Blooming season: Starts blooming the first year from cuttings and blooms year round.

Flowers:

*Color.*—White.

*Petalage.*—Double.

Foliage:

*Color.*—Generally green to bluish-green Plate XVIII–*i*–33′, winter green to plate XIX–*x*–39′, dark cinnabar green with the more recently sprouted portions a lighter shade of green.

*Size.*—The size of the flowers and foliage is the same as commercial carnation varieties for both "standards" and "miniatures."

We claim:

1. A new and distinct variety of carnation plant as herein disclosed, characterized as to novelty by a white, quilled petal structure.

No references cited.

ROBERT E. BAGWILL, *Primary Examiner.*